(12) United States Patent
Hung et al.

(10) Patent No.: US 9,416,346 B2
(45) Date of Patent: Aug. 16, 2016

(54) METHOD OF DAMAGING CELL STRUCTURE OF AQUATIC SUBSTANCE

(71) Applicant: METAL INDUSTRIES RESEARCH & DEVELOPMENT CENTRE, Kaohsiung (TW)

(72) Inventors: Chun-Hung Hung, Kaohsiung (TW); Chi-Hui Chen, Kaohsiung (TW); Ching-Jui Tsai, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 3 days.

(21) Appl. No.: 14/555,137

(22) Filed: Nov. 26, 2014

(65) Prior Publication Data

US 2015/0159129 A1    Jun. 11, 2015

(30) Foreign Application Priority Data

Dec. 11, 2013   (TW) .............................. 102145712 A
Jul. 29, 2014   (CN) .......................... 2014 1 0366022

(51) Int. Cl.
   *C12N 1/06*   (2006.01)
(52) U.S. Cl.
   CPC ..................................... *C12N 1/066* (2013.01)
(58) Field of Classification Search
   None
   See application file for complete search history.

(56) References Cited

U.S. PATENT DOCUMENTS 7,763,724 B2      7/2010 Kang et al.
2011/0183403 A1*  7/2011 Dierkes .................... C11B 1/06
                                               435/257.1

FOREIGN PATENT DOCUMENTS

TW            201122092        7/2011

OTHER PUBLICATIONS

Lin et al. "Disintegration of yeast cells by pressurized carbon dioxide", Biotechnology Progress 7 (3): 201-204, 1991.*
Enomoto et al. "Inactivation of food microorganisms by high-pressure carbon dioxide treatment with or without explosive decompression." Bioscience, Biotechnology, and biochemistry 61(7): 1133-1137, 1997.*
Translation for the Search Report issued on Nov. 18, 2014 by TIPO for the corresponding TW Patent Application No. 102145712.

* cited by examiner

*Primary Examiner* — Emily Cordas
(74) *Attorney, Agent, or Firm* — WPAT, P.C., Intellectual Property Attorneys; Anthony King

(57) ABSTRACT

A method of damaging cell structure of an aquatic substance includes: providing an aquatic substance raw material, where the aquatic substance raw material includes an aquatic substance; adjusting a water content in the aquatic substance raw material to form an aquatic substance slurry to be processed; placing the aquatic substance slurry to be processed in a pressure container; introducing a compressed gas into the pressure container to enable the compressed gas and the water in the aquatic substance slurry to be processed to form an acidic fluid, and making the cell structure of the aquatic substance hydrolyzed and damaged by the acidic fluid; and performing a depressurizing step to separate the compressed gas.

16 Claims, 4 Drawing Sheets

METHOD OF DAMAGING CELL STRUCTURE OF AQUATIC SUBSTANCE

FIELD

The disclosure relates to a method of damaging cell structure, more particular to a method of damaging cell structure of an aquatic substance.

BACKGROUND

Aquatic substance such as algae has nowadays become popular sources of biomass energy, food, feed, and medicines, because the aquatic substance grows rapidly and absorbs carbon dioxide to achieve carbon fixation. After photosynthesis, algae can store energy in the form of protein, carbohydrate or oil and fat. Algae and fungi are rich in health care constituents such as β-carotene, chlorophyll, linolenic acid, phycocyanin, vitamins, and carbohydrate and have desirable effects in terms of medical care and health care. However, before constituents in algae and fungi are eaten, extracted, and hydrolyzed, the cell structures of algae and fungi usually need to be damaged to increase an absorption rate, an extraction rate or a hydrolysis rate.

Existing methods of damaging a cell structure are analyzed by using the following technical patent documents.

1. TW542699

Approach: A gas having a pressure between 2 kg/cm$^2$ and 10 kg/cm$^2$ and a temperature between 100° C. to 150° C. is used to enable water molecules inside a cell to reach a liquid-vapor critical point and produce an instantaneous pressure drop to enable gasification of water molecules inside the cell to break a cell wall.

Disadvantages: Use of a high temperature process and high energy consumption; easy damage and decomposition of active constituents contained in a cell at a high temperature; and occurrence of explosive noise in the process.

2. U.S. Pat. No. 7,763,724

Approach: Under conditions of a liquid pressure between 500 MPa and 1000 MPa and a temperature between 60° C. and 80° C., the cell structures of aquatic algae are liquefied to produce glucose.

Disadvantage: The operating condition is an ultra high pressure above 500 MPa, and therefore equipment with a thick and heavy pressure-bearing structure is required for processing; the equipment has high building and maintenance cost, making it difficult for scaled-up use of the process for commercial operation.

Based on the analysis above, it is necessary to provide a method of damaging cell structure of an aquatic substance, so as to solve the foregoing deficiencies in the prior art.

SUMMARY OF THE INVENTION

In accordance with one aspect of the present disclosure, a method of damaging cell structure of an aquatic substance includes step in which an aquatic substance raw material is provided, where the aquatic substance raw material includes an aquatic substance. The method continues with step in which a water content in the aquatic substance raw material is adjusted to form an aquatic substance slurry to be processed. The method continues with step in which the aquatic substance slurry to be processed is placed in a pressure container. The method continues with step in which a compressed gas is introduced into the pressure container to enable the compressed gas and the water in the aquatic substance slurry to be processed to form an acidic fluid, and makes the cell structure of the aquatic substance hydrolyzed and damaged by the acidic fluid. The method continues with step in which a depressurizing step is performed to separate the compressed gas.

The method of the present disclosure can be operated at a low-temperature environment, so that energy consumption can be reduced and active constituents contained in cells can be prevented from damage and decomposition at a high temperature. In addition, the present disclosure can be implemented at a relatively low pressure condition; therefore, the use of thick and heavy high pressure equipment is not required, the building and maintenance cost of the equipment can be significantly reduced, and the present disclosure is applicable to scaled-up use of the process for commercial operation.

BRIEF DESCRIPTION OF THE DRAWINGS

Aspects of the present disclosure are understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION OF THE INVENTION

Figure 1:
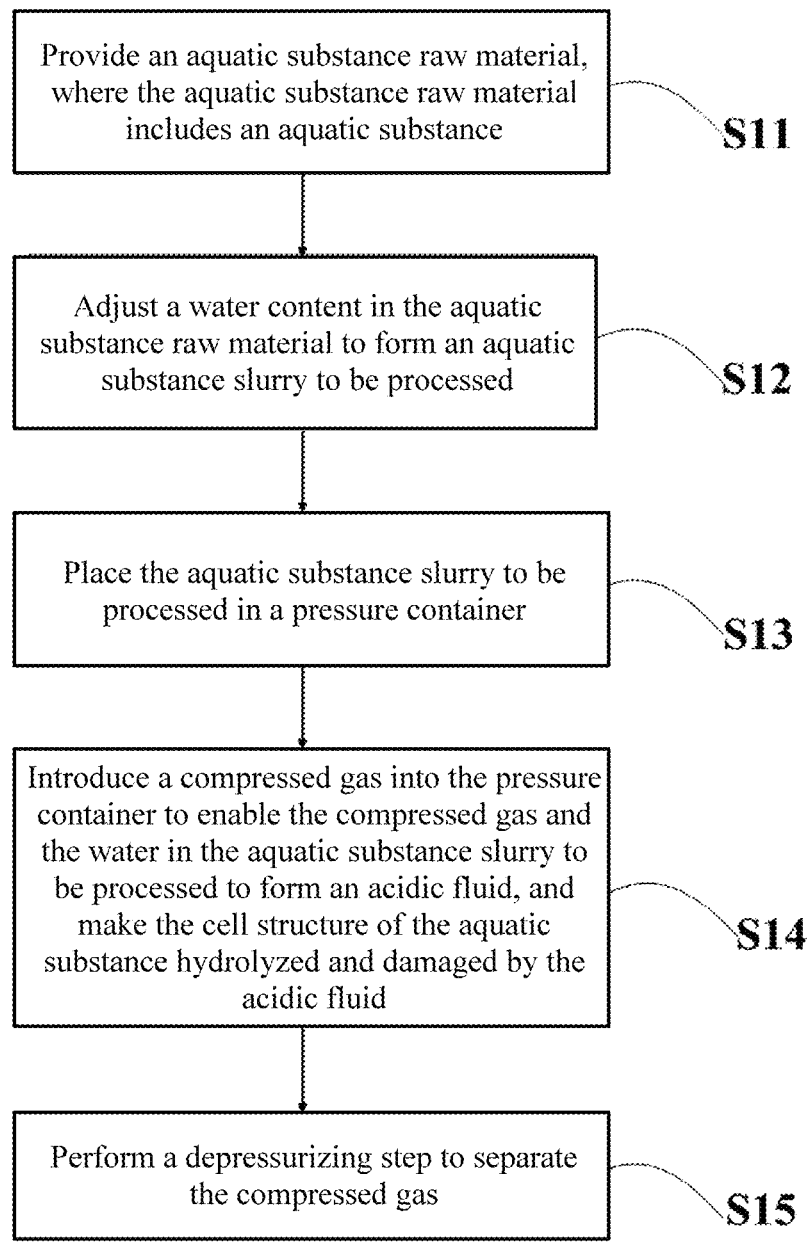
FIG. 1 is a flow diagram of a method of damaging cell structure of an aquatic substance according to the present disclosure.

It is to be understood that the following disclosure provides many different embodiments or examples, for implementing different features of various embodiments. Specific examples of components and arrangements are described below to simplify the present disclosure. The present disclosure may, however, be embodied in many different forms and should not be construed as being limited to the embodiments set forth herein; rather, these embodiments are provided so that this description will be thorough and complete, and will fully convey the present disclosure to those of ordinary skill in the art. It will be apparent, however, that one or more embodiments may be practiced without these specific details.

In addition, the present disclosure may repeat reference numerals and/or letters in the various examples. This repetition is for the purpose of simplicity and clarity and does not in itself dictate a relationship between the various embodiments and/or configurations discussed.

It will be understood that singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 is a flow diagram of a method of damaging cell structure of an aquatic substance according to the present disclosure. Referring to Step S11 in FIG. 1, an aquatic substance raw material is provided, where the aquatic substance raw material includes an aquatic substance. The aquatic substance can be one selected from the following: algae and fungi.

In this step, the algae can be one selected from the following: microalgae and aquatic algae. Preferably, the size range of microalgae is 3 micrometers to 30 micrometers inclusive, and the microalgae can be one selected from the following: green algae, diatoms, spirulina, marimo, and cryptomonadales. A culture concentration of the microalgae is usually smaller than 0.3 wt %; through water removal measures such as centrifugal dewatering and drying, the concentration can exceed 25 wt %. An excessively low or excessively high concentration is not suitable for processing of damaging cell structure with a compressed gas.

Referring to Step S12, a water content in the aquatic substance raw material is adjusted to form an aquatic substance slurry to be processed. When the original aquatic substance raw material contains a large amount of water, a manner of adjusting a water content is to reduce the water content in the aquatic substance raw material, so as to adjust a weight percent concentration of the aquatic substance slurry to 0.4 wt % to 25 wt % inclusive, making gas diffuse easily. The method of reducing a water content can be one selected from the following: sedimentation, centrifugation, and filtering. However, when the original aquatic substance raw material contains an excessively small amount of water, a manner of adjusting a water content is to increase the water content in the aquatic substance raw material.

Referring to Step S13, the aquatic substance slurry to be processed is placed in a pressure container. In this step, to increase a processing area of the aquatic substance slurry to be processed in the pressure container, the aquatic substance slurry to be processed forms an aquatic substance film in the pressure container. The method of forming the aquatic substance film can be one selected from the following: a knife coating method and a spray coating method. Meanwhile, preferably, a thickness of the aquatic substance film is smaller than or equal to 2 centimeters.

Referring to Step S14, a compressed gas is introduced into the pressure container to enable the compressed gas and the water in the aquatic substance slurry to be processed to form an acidic fluid, and makes the cell structure of the aquatic substance hydrolyzed and damaged by the acidic fluid. In this step, the compressed gas and the water in the aquatic substance slurry to be processed form an acidic fluid to contact cells of the aquatic substance to facilitate degradation and damage of the cell structure. In addition, the concentration of the compressed gas in the water gradually increases with time and a pH value of the acidic fluid decreases. Preferably, the pH value of the acidic fluid is 2 to 6.5 inclusive, while an operating temperature in the pressure container is lower than or equal to 55° C.

In this step, the compressed gas includes one or a combination of two of carbon dioxide, methane, and nitrogen. In addition, a gauge pressure of the compressed gas is greater than or equal to 10 bars, so as to control the pH value of the acidic fluid between 2 and 6.5 inclusive, and a time of keeping the pressure of the compressed gas is not shorter than 1 minute. Preferably, the gauge pressure of the compressed gas is 30 bars to 200 bars inclusive, and the time of keeping the pressure of the compressed gas is 15 minutes to 48 hours inclusive.

In addition, the hydrolysis of the cell structure of the aquatic substance can be accelerated and a wall damage rate can be increased by increasing the amount of the acidic fluid. Therefore, in this step, a pressurizing liquid can be introduced into the pressure container, so as to increase an internal pressure of the pressure container, and makes the cell structure of the aquatic substance is pressed and damaged. Furthermore, the pressure of the pressurizing liquid can be changed to produce an effect of repeatedly applying a stress on the cell structure of the aquatic substance, which can also accelerate the damage of the cell structure.

In this step, the pressurizing liquid includes one or a combination of several of water, methanol, ethanol, and vegetable oil. In addition, the pressure of the pressurizing liquid is greater than or equal to the pressure of the compressed gas, and a time of keeping the pressure of the pressurizing liquid is not shorter than 1 minute. Preferably, a gauge pressure of the pressurizing liquid is 100 bars to 4000 bars inclusive, and the time of keeping the pressure of the pressurizing liquid is 15 minutes to 48 hours inclusive.

Referring to Step S15, a depressurizing step is performed to separate the compressed gas. In the depressurizing step, the pressure in the pressure container is reduced to a gauge pressure of zero and the depressurizing time is not shorter than 1 minute, so as to vaporize and separate the compressed gas for further recycling.

The method of the present disclosure can be operated at a low-temperature environment, so that energy consumption can be reduced and active constituents contained in cells can be prevented from damage and decomposition at a high temperature. In addition, the present disclosure can be implemented at a relatively low pressure condition; therefore, the use of thick and heavy high pressure equipment is not required, the building and maintenance cost of the equipment of the present disclosure can be significantly reduced, and the present disclosure is applicable to scaled-up use of the process for commercial operation.

Contrast Example 1

Figure 2:
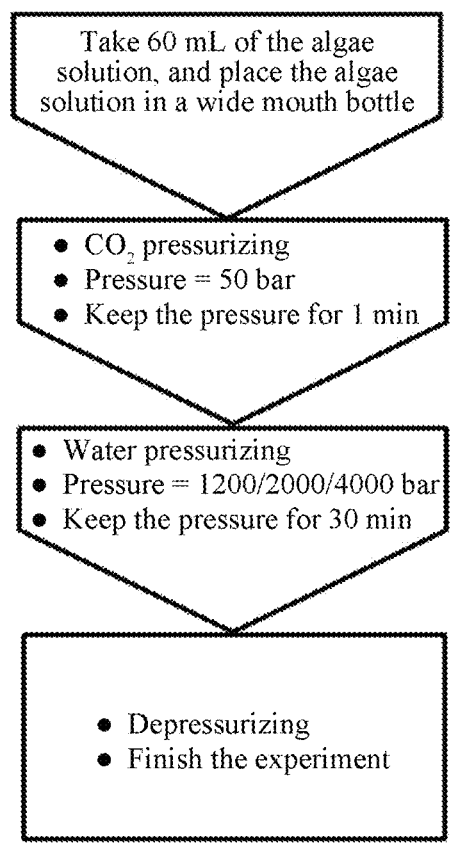
FIG. 2 is a flow diagram of an experiment of Contrast Example 1.

Referring to FIG. 2, FIG. 2 is a flow diagram of an experiment of Contrast Example 1. In the Contrast Example 1, the aquatic substance raw material is an algae solution (the concentration is about 0.05 wt % to 0.1 wt %), the compressed gas is carbon dioxide ($CO_2$), and the pressurizing liquid is water.

This contrast example provides a method of damaging cell structure of an aquatic substance, and the specific steps are as follows:

Step 1: Take 60 milliliters of the algae solution, and place the algae solution in a wide mouth bottle.

Step 2: Place the foregoing algae solution in a pressure container.

Step 3: Introduce $CO_2$ having a gauge pressure of 50 bars into the pressure container, and keep the pressure for 1 minute, where the experiment temperature is 30° C.

Step 4: Introduce water having gauge pressures being 1200 bars, 2000 bars, and 4000 bars respectively into the pressure container, and keep the pressure for 30 minutes.

Step 5: Perform depressurizing to finish the experiment.

Embodiment 1

Figure 3:
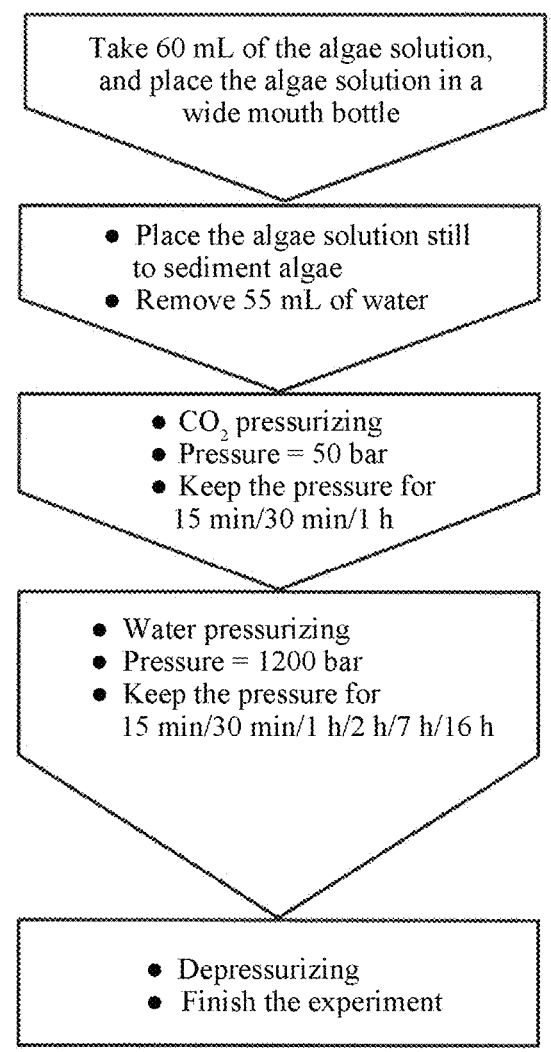
FIG. 3 is a flow diagram of an experiment of Embodiment 1.

Referring to FIG. 3, FIG. 3 is a flow diagram of an experiment of Embodiment 1. In Embodiment 1, the aquatic substance raw material is an algae solution (the concentration is about 0.05 wt % to 0.1 wt %), the compressed gas is carbon dioxide ($CO_2$), and the pressurizing liquid is water.

This embodiment provides a method of damaging cell structure of an aquatic substance, and the specific steps are as follows:

Step 1: Take 60 milliliters of the algae solution, and place the algae solution in a wide mouth bottle.

Step 2: Place the foregoing algae solution still for 0.5 hour, enable algae to sediment at the bottom of the wide mouth bottle, and then remove 55 milliliters of water to form algae slurry.

Step 3: Place the foregoing algae slurry in a pressure container, and enable the algae slurry to form a film on an inner wall of the pressure container.

Step 4: Introduce $CO_2$ having a gauge pressure of 50 bars into the pressure container, and keep the pressure for 15 minutes, 30 minutes, and 1 hour, respectively, where the experiment temperature is 30° C.

Step 5: Introduce water having a gauge pressure of 1200 bars into the pressure container, and keep the pressure for 15 minutes, 30 minutes, 1 hour, 2 hours, 7 hours, and 16 hours, respectively.

Step 6: Perform depressurizing to finish the experiment.

Embodiment 2

This embodiment provides a method of damaging cell structure of an aquatic substance, and the specific steps are as follows:

The experimental conditions in Embodiment 2 are basically the same as those in Embodiment 1, and the differences only lie in that Step 5 in Embodiment 1 is omitted in Embodiment 2, and the time of keeping the pressure in Step 4 is set to 20 minutes, 1 hour, and 2 hours.

Contrast Example 2

This contrast example provides a method of damaging cell structure of an aquatic substance, and the specific steps are as follows:

The experimental conditions in Contrast Example 2 are basically the same as those in Embodiment 1, and the differences only lie in that Step 4 in Embodiment 1 is omitted in Contrast Example 2, and the time of keeping the pressure in Step 5 is set to 1 hour, 2 hours, and 4 hours.

As an electrolyte flows out after algae cells are damaged, and a cell wall damage rate of the algae cells shows positive correlation to electric conductivity. Therefore, in this embodiment, to learn damage conditions of algae cells in Contrast Example 1, Embodiment 1, Embodiment 2, and Contrast Example 2, wall damage rates are measured by using an electric conductivity method and the measurement results are shown in Table 1.

TABLE 1

Measurement Results of Wall Damage Rates in Contrast Example 1, Embodiment 1, Embodiment 2, and Contrast Example 2

| | | Algae/Water Separation | $CO_2$ Pressurizing Pressure | $CO_2$ Pressurizing Pressure Keeping | Water Pressurizing Pressure | Water Pressurizing Pressure keeping | Wall Damage Rate |
|---|---|---|---|---|---|---|---|
| Contrast Example 1 | 1-1 | None | 50 bars | 1 minute | 1200 bars | 30 minutes | 30% |
| | 1-2 | | | | 2000 bars | 30 minutes | 30% |
| | 1-3 | | | | 4000 bars | 30 minutes | 27% |
| Embodiment 1 | 2-1 | Remove 55 milli- | 50 bars | 15 minutes | 1200 bars | 15 minutes | 84% |
| | 2-2 | | | 30 minutes | 1200 bars | 30 minutes | 85% |
| | 2-3 | liters of water | | 1 hour | 1200 bars | 1 hour | 85% |
| | 2-4 | | | | 1200 bars | 2 hours | 85% |
| | 2-5 | | | | 1200 bars | 7 hours | 92% |
| | 2-6 | | | | 1200 bars | 16 hours | 95% |
| Embodiment 2 | 3-1 | Remove 55 milli- liters of water | 50 bars | 20 minutes | None | | 26% |
| | 3-2 | | 50 bars | 1 hour | | | 52% |
| | 3-3 | | 50 bars | 2 hours | | | 78% |
| Contrast Example 2 | 4-1 | Remove 55 milli- liters of water | None | | 1200 bars | 1 hour | 9% |
| | 4-2 | | | | 1200 bars | 2 hours | 17% |
| | 4-3 | | | | 1200 bars | 4 hours | 16% |

Figure 4:
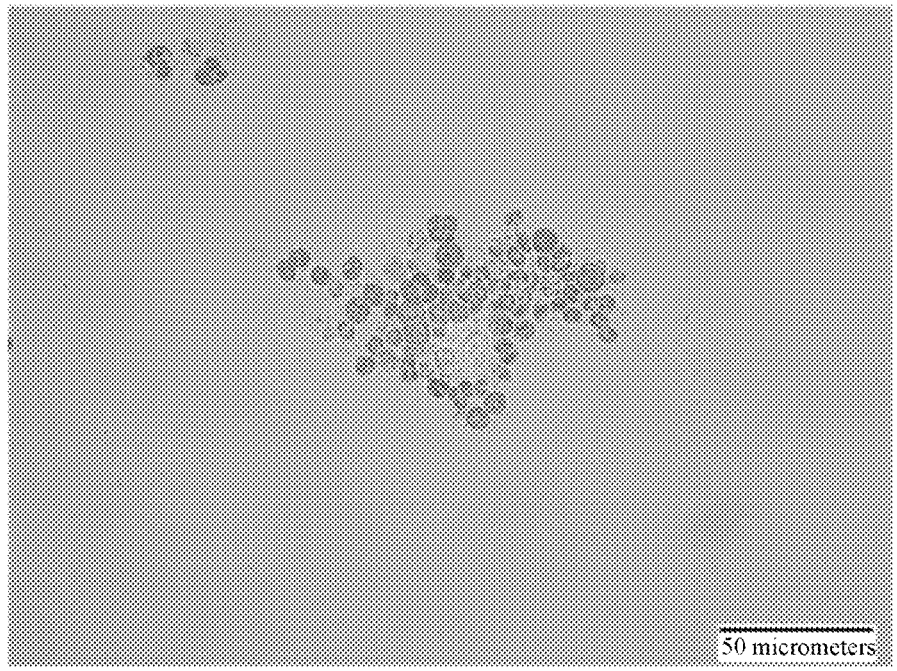
FIG. 4 is an electron micrograph after walls of the algae cells are damaged in Contrast Example 1.

The results in Table 1 show that in Contrast Example 1, without the removal of 55 milliliters of water (about 92% of the volume of the algae solution), the wall damage rate of the algae cells is only 30%. The reason that the wall damage rate in Contrast Example 1 is low lies in that the pH value of the algae solution is about 9 (equivalent to an alkaline fluid), and in the case that the algae solution contains a large amount of alkaline fluid, $CO_2$ does not diffuse easily, and it is difficult to form the carbonic acid. Referring to FIG. 4, FIG. 4 is an electron micrograph after walls of the algae cells are damaged in Contrast Example 1. As shown in FIG. 4, in Contrast Example 1, an oil drop flowing phenomenon after the walls of the algae cells are damaged is not obvious.

In contrast, after 55 milliliters of water is removed in Embodiment 1, $CO_2$ diffuses easily and the carbonic acid is formed easily; under the condition of water pressurizing in combination, the wall damage rate of the algae cells can reach 95%; even though the water pressurizing step is omitted, the wall damage rate of the algae cells can still reach 78% (Embodiment 2).

Figure 5:
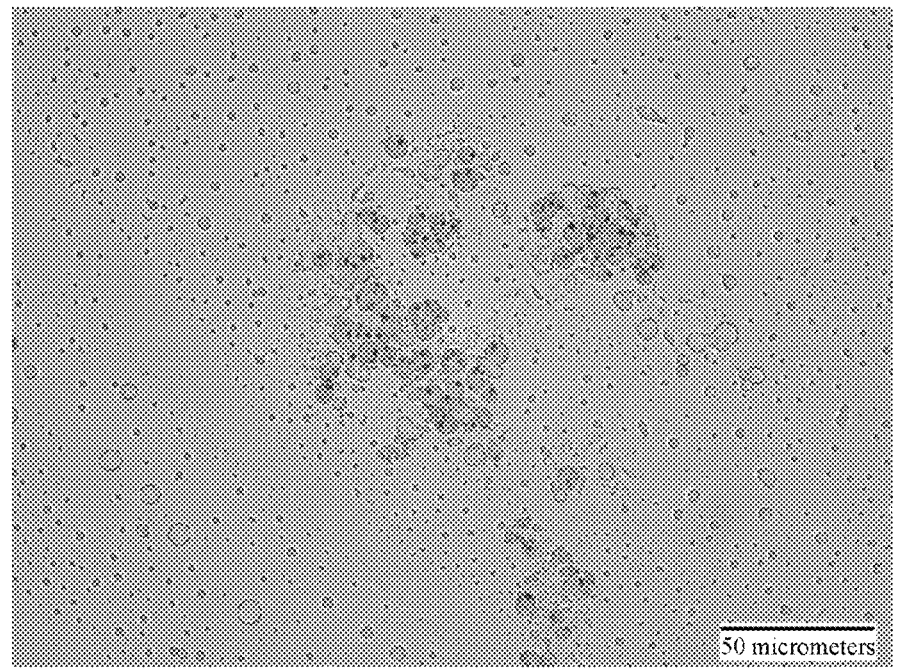
FIG. 5 is an electron micrograph after the walls of the algae cells are damaged in Embodiment 1.

Referring to FIG. 5, FIG. 5 is an electron micrograph after the walls of the algae cells are damaged in Embodiment 1. As shown in FIG. 5, an oil drop flowing phenomenon after the walls of the algae cells are damaged in Embodiment 1 is very obvious.

In addition, the results in Contrast Example 2 show that if the $CO_2$ pressurizing step is omitted, the carbonic acid cannot be formed, making it impossible to hydrolyze and damage the algae cells; even though the water pressurizing step is further performed, the wall damage rate of the algae cells in Contrast Example 2 can only reach 16%.

The original aquatic substance raw material in the foregoing embodiments contains a large amount of water, and therefore, a manner of reducing a water content requires to be adopted to adjust a water content in the aquatic substance raw material to form aquatic substance slurry to be processed. However, when the original aquatic substance raw material contains an excessively small amount of water, aquatic substance slurry becomes excessively thick and lacks water; in this case, a manner of increasing a water content requires to be adopted to adjust a water content in the aquatic substance raw material, thereby helping form a substance film and increase a wall damage rate.

Moreover, the scope of the present application is not intended to be limited to the particular embodiments of the process, machine, manufacture, and composition of matter, means, methods and steps described in the specification. As those skilled in the art will readily appreciate form the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure.

Accordingly, the appended claims are intended to include within their scope such processes, machines, manufacture, and compositions of matter, means, methods or steps. In addition, each claim constitutes a separate embodiment, and the combination of various claims and embodiments are within the scope of the invention.

What is claimed is:

1. A method of damaging cell structure of an aquatic substance, comprising:
   (a) providing an aquatic substance raw material, where the aquatic substance raw material includes an aquatic substance;
   (b) adjusting a water content in the aquatic substance raw material to form an aquatic substance slurry to be processed;
   (c) placing the aquatic substance slurry to be processed in a pressure container, and enabling the aquatic substance slurry to be processed to form an aquatic substance film in the pressure container;
   (d) introducing a compressed gas into the pressure container to enable the compressed gas and the water in the aquatic substance slurry to be processed to form an acidic fluid, and making the cell structure of the aquatic substance hydrolyzed and damaged by the acidic fluid; and
   (e) performing a depressurizing step to separate the compressed gas.

2. The method of claim 1, wherein a weight percent concentration of the aquatic substance slurry of the step (b) is 0.4 wt % to 25 wt % inclusive.

3. The method of claim 1, wherein the step (b) further comprises reducing the water content in the aquatic substance raw material.

4. The method of claim 1, wherein the step (b) further comprises increasing the water content in the aquatic substance raw material.

5. The method of claim 1, wherein a thickness of the aquatic substance film is smaller than or equal to 2 centimeters.

6. The method of claim 1, wherein a gauge pressure of the compressed gas of the step (d) is greater than or equal to 10 bars.

7. The method of claim 6, wherein the gauge pressure of the compressed gas is 30 bars to 200 bars inclusive.

8. The method of claim 6, wherein the time of keeping the pressure of the compressed gas is 15 minutes to 48 hours inclusive.

9. The method of claim 1, wherein the depressurizing time of the step (e) is not shorter than 1 minute.

10. The method of claim 1, wherein an operating temperature in the pressure container of the step (d) is lower than or equal to 55° C.

11. The method of claim 1, wherein a pH value of the acidic fluid is 2 to 6.5 inclusive.

12. The method of claim 1, wherein the step (d) further comprises introducing a pressurizing liquid into the pressure container, so as to make the cell structure of the aquatic substance is pressed and damaged.

13. The method of claim 12, wherein the pressure of the pressurizing liquid is greater than or equal to the pressure of the compressed gas.

14. The method of claim 13, wherein a gauge pressure of the pressurizing liquid is 100 bars to 4000 bars inclusive.

15. The method of claim 14, wherein a time of keeping the pressure of the pressurizing liquid is not shorter than 1 minute.

16. The method of claim 15, wherein the time of keeping the pressure of the pressurizing liquid is 15 minutes to 48 hours inclusive.

* * * * *